US012758639B2

(12) United States Patent
Nau et al.

(10) Patent No.: US 12,758,639 B2
(45) Date of Patent: Oct. 13, 2026

(54) USE OF A BORON CLUSTER AS TRANSMEMBRANE CARRIER

(71) Applicants: CONSTRUCTOR UNIVERSITY BREMEN GGMBH, Bremen (DE); UNIVERSIDADE DE SANTIAGO DE COMPOSTELA, Santiago de Compostela (ES)

(72) Inventors: Werner Nau, Bremen (DE); Javier Montenegro, Santiago de Compostela (ES)

(73) Assignees: UNIVERSIDADE DE SANTIAGO DE COMPOSTELA, Santiago de Compostela (ES); CONSTRUCTOR UNIVERSITY BREMEN GGMBH, Bremen (DE)

( * ) Notice: Subject to any disclaimer, the term of this patent is extended or adjusted under 35 U.S.C. 154(b) by 662 days.

(21) Appl. No.: 18/011,533

(22) PCT Filed: Jun. 11, 2021

(86) PCT No.: PCT/EP2021/065748
§ 371 (c)(1),
(2) Date: Dec. 20, 2022

(87) PCT Pub. No.: WO2021/259668
PCT Pub. Date: Dec. 30, 2021

(65) Prior Publication Data

US 2023/0293699 A1 Sep. 21, 2023

(30) Foreign Application Priority Data

Jun. 26, 2020 (EP) .................................... 20182648

(51) Int. Cl.
*A61K 47/52* (2017.01)

(52) U.S. Cl.
CPC .................................... *A61K 47/52* (2017.08)

(58) Field of Classification Search
CPC .... A61K 47/52; A61K 31/7036; A61K 47/02; A61P 31/04; A61P 35/00
See application file for complete search history.

(56) References Cited

FOREIGN PATENT DOCUMENTS

CZ 2018-331 A3 1/2020

OTHER PUBLICATIONS

Axtell et al. Inorg Chem. 2018; 57: 2333-2350. (Year: 2018).*
K. Fink et al.; "Metallacarboranes as a tool for enhancing the activity of therapeutic peptides", Annals of the New York Academy of Sciences, vol. 1457, pp. 128-141 (2019).
K. I. Assaf et al.: "Face-Fusion of Icosahedral Boron Hydride Increases Affinity to γ-Cyclodextrin: closo,closo-$[B_{21}H_{18}]^-$ as an Anion with Very Low Free Energy of Dehydration", vol. 21, pp. 971-976 (2020).
K, I. Assaf et al.: The Chaotropic Effect as an Assembly Motif in Chemistry, Angewandte Chemie, vol. 57, pp. 13968-13981 (2018).
K. I. Assaf et al.: "Dodecaborate-Functionalized Anchor Dyes for Cyclodextrin-Based Indicator Displacement Applications", Organic Letters, vol. 18, pp. 932-935 (2016).
S. El Anwar et al.: Versatile, one-pot introduction of nonahalogenated 2-ammonio-decaborate ions as boron cluster scaffolds into organic molecules; host-guest complexation with γ-cyclodextrin, Chem, Commun., vol. 55, pp. 13669-13672 (2019).

* cited by examiner

*Primary Examiner* — David Browe
(74) *Attorney, Agent, or Firm* — Norman B. Thot

(57) ABSTRACT

A method of treating cancer in a subject in need thereof. The method includes providing an anticancer drug which is cationic, zwitterionic or not charged, providing a boron cluster which is halogenated, mixing the boron cluster and the anticancer drug so that the boron cluster and the anticancer drug together form a non-covalent complex mixture, and administering the non-covalent complex mixture to the subject so that the boron cluster acts as a transmembrane carrier to transport the anticancer drug across a membrane of a cell or a vesicle in the subject. The boron cluster has a globular shape or an ellipsoidal shape. The boron cluster is a mononuclear boron cluster. The boron cluster is free of a pendant group, the pendant group being defined as any group which is linked to a core of the boron cluster except for hydrogen, a halogen, a methyl, and/or the anticancer drug.

5 Claims, 5 Drawing Sheets

USE OF A BORON CLUSTER AS TRANSMEMBRANE CARRIER

CROSS REFERENCE TO PRIOR APPLICATIONS

This application is a U.S. National Phase application under 35 U.S.C. § 371 of International Application No. PCT/EP2021/065748, filed on Jun. 11, 2021 and which claims benefit to European Patent Application No. 20182648.4, filed on Jun. 26, 2020. The International Application was published in English on Dec. 30, 2021 as WO 2021/259668 A1 under PCT Article 21(2).

FIELD

The present invention relates to the use of a boron cluster as a transmembrane carrier to transport a bioactive molecule across a membrane.

BACKGROUND

For medical or biological agents to be effective, they must reach their biomolecular target, which is usually located inside the cell. The agent must thus penetrate the cell membrane, which forms a natural barrier against foreign substances. For penetration, either the active ingredients may be chemically modified, which often changes or weakens the agent's effect, or additives can be added, which serve as carriers (counterion activators) through the membrane. Such effective transporters are commercially applied in medicine and pharmacy, but they are also commonly used in cell biology and basic research. Membrane transport and intracellular delivery constitutes a major bottleneck for the discovery and application of new therapeutics and bioactive compounds in drug delivery and molecular biology.

As transporters, a frequently applied strategy is the use of organic cationic molecules with aromatic or aliphatic hydrophobic moieties, which enhance multivalent interactions with the cell membrane and thereby trigger the translocation of the cargo. However, these carriers and their cargo complexes usually enter cells by endocytosis, which hinders the intracellular targeting of the cargo. Elaborate strategies have been developed as a remedy, such as the introduction of hydrophobic carbon tails, the coupling with membrane-lytic peptides, the development of pH-sensitive peptides (e.g., GALA) or the use of strongly amphiphilic peptides and polymers.

A possible alternative to by-pass the interference of endosomal entrapment is the use of anionic amphiphilic activators. These activators neutralize the charge of cationic carriers and increase their hydrophobicity, which switches their endosomal uptake to direct membrane translocation. However, the amphiphilic transporters currently used to transport cationic agents have several disadvantages: Many precipitate the agents when they are mixed in solution, so that the transporter must be added first; this is not feasible for pharmaceuticals. Although many transporters promote the uptake of the agents, this often occurs by an endosomal transport mechanism that may not lead to the release of the agents in the cytosol, but instead transports the active ingredients out of the cell. Many carriers can only be applied to a small number of compounds. Due to the transporters' amphiphilicity (they contain a hydrophobic group), the transporters are furthermore only slightly water soluble. For positively charged and neutral compounds, for example, to introduce antimicrobial peptides into cells, only a few transporters are thus far available.

CZ 2018331 A3 describes an RNA transport complex based on a boron cluster and hydrazone derivatives conjugated to a guanidinium group that is useful primarily as a transport system of DNA/RNA strands or fragments through model biological membranes as a therapeutic tool for targeting a drug for tumor immunotherapy, wherein the negatively charged RNA strand is in particular transported by the positively charged guanidinium group, as an established recognition motif for anionic DNA/RNA phosphate groups, covalently attached to the boron cluster.

Krysztof Fink et al. (Krzysztof Fink et al, Annals of the New York Academy of Sciences, vol. 1457, no. 1, 2019-08-12, pages 128-141, XP055755378), in the Introduction of the article (end of first paragraph on page 129), formulate the hypothesis that conjugation of peptides with a binuclear boron cluster may increase their ability to cross biological membranes, while the results only show that for a particular peptide, thymosin (β4(Tβ4), the covalent attachment of 1,4-dioxane-based oxonium derivatives of a binuclear boron cluster to a specific domain, the actin-binding one, is required to induce an enhanced wound-closure effect, which leads the authors to the suggestion that the binuclear boron cluster is involved in the formation of interactions with molecular targets of Tβ4. No evidence is given for an enhanced ability of the described conjugates to cross biological membranes.

SUMMARY

An aspect of the present invention is to provide a method which allows a transport of compounds inside of cells and/or vesicles, but which overcomes the above described shortcomings, in particular avoiding precipitation, allowing or circumventing endosomal escape, and allowing for a transport of various substance classes with one type of carrier to avoid the need for optimization.

In an embodiment, the present invention provides a method of using a boron cluster as a transmembrane carrier to transport a bioactive molecule across a membrane of a cell or a vesicle. The method includes providing a boron cluster comprising at least one of at least one hydrogen atom and at least one halogen atom, providing a bioactive molecule which is cationic, zwitterionic or not charged, so that the bioactive molecule is not negatively charged, and using the boron cluster as a transmembrane carrier to transport the bioactive molecule across the membrane of the cell or the vesicle.

BRIEF DESCRIPTION OF THE DRAWINGS

The present invention is described in greater detail below on the basis of embodiments and of the drawings in which.

DETAILED DESCRIPTION

Figure 1:
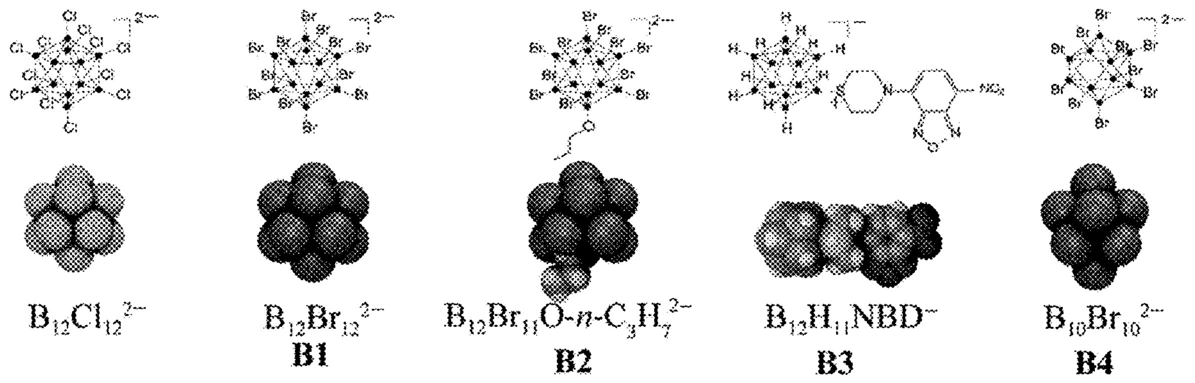
FIG. 1 shows chemical structures (top, •=Boron) and space-filling molecular models (bottom) of dodecaborate ($B_{12}X_{12}^{2-}$) and decaborate ($B_{10}Br_{10}^{2-}$) clusters, and selected derivatives, whereas particularly effective boron clusters are marked with B1 to B4.
Figure 2:
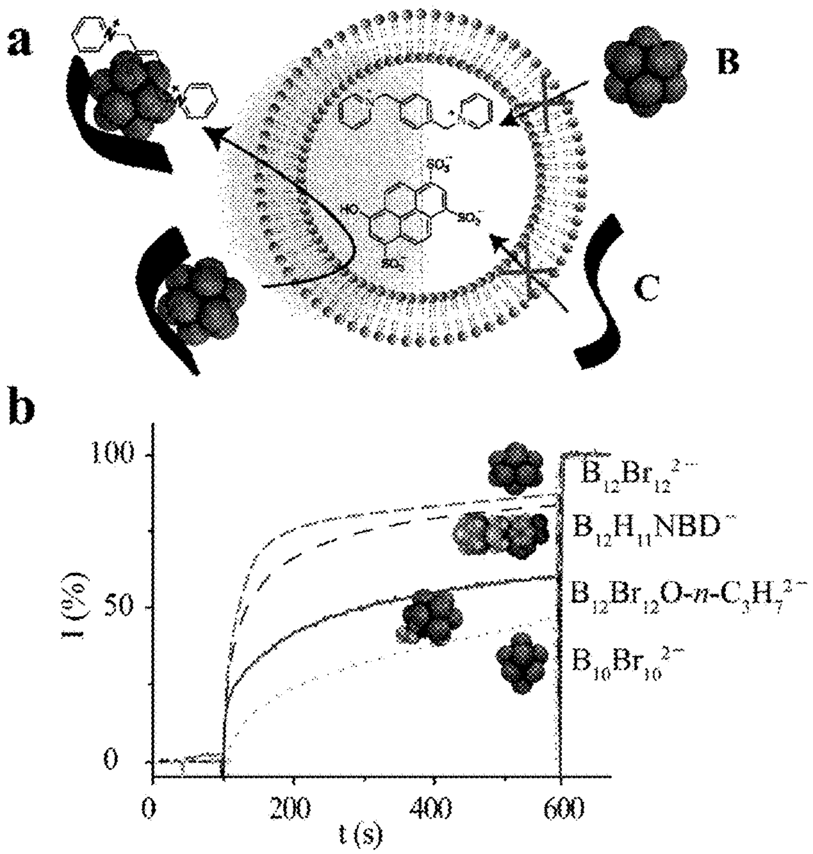
FIG. 2 shows: a, a schematic representation of the transport of otherwise impermeable analytes facilitated by superchaotropic anions with encapsulated HPTS/DPX probe/quencher pair employed for signaling (B: Boron Cluster, C: Impermeable cargo); and b, Changes in HTPS emission ($\lambda_{ex}$=413 nm, $\lambda_{em}$=511 nm) in EYP⊃DHPTS/DPX (13 μM phospholipids) as a function of time during the addition of carriers B1-4 (namely: B1: $B_{12}Br_{12}^{2-}$, B2: $B_{12}Br_{11}$—O-n-$C_3H_7^{2-}$, B3: $B_{12}H_{11}NBD^-$, and B4: $B_{10}Br_{10}^{2-}$); clusters (150 μM) added at t=50 s, heptaarginine (20 μM) at t=100 s, and TX-100 at t=600 s, for calibration; (I (%): Fluorescence intensity normalize to 100%, t(s): time in seconds)
Figure 3:
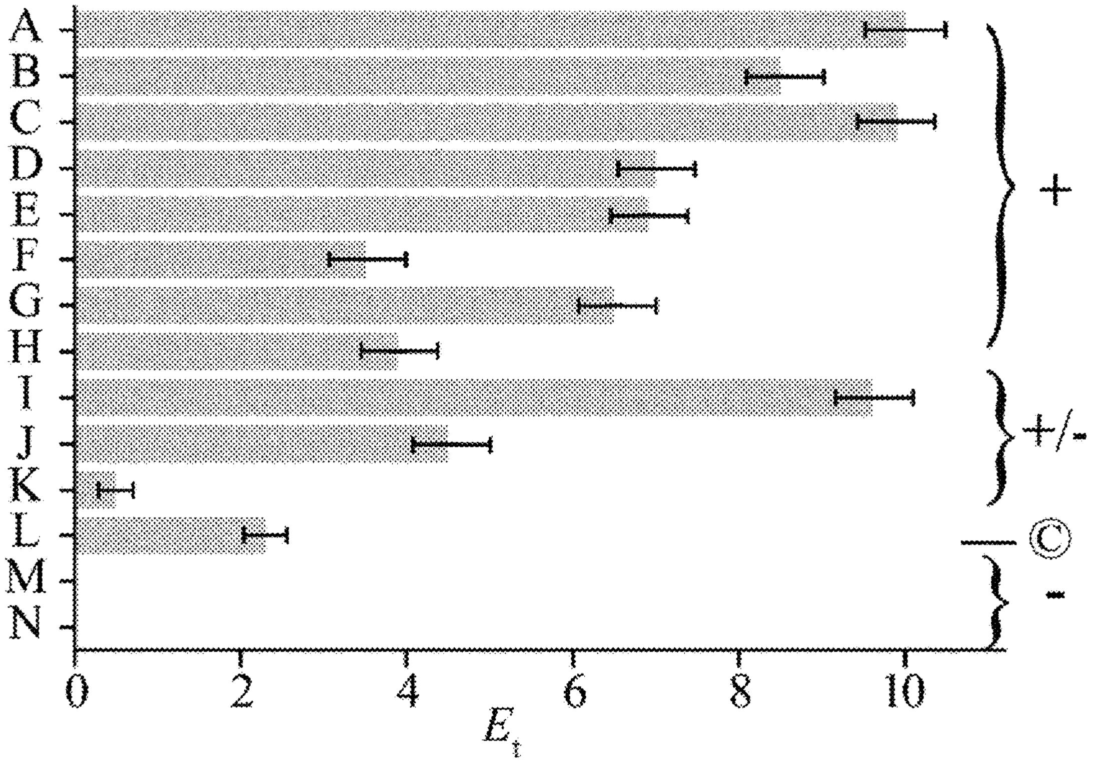
FIG. 3 shows the transport efficiency of B1 towards selected impermeable analytes of biological/clinical relevance; error bars refer to standard deviation. A: Heptaarginine, B: Heptalysine, C: Protamine, D: Acethylcholine, E: Pancuronium, F: Vecuronium, G: Vitamin B1, H: Ranitidin, I: Tryptophan, J: Ampicilin, K: Phenylalanine, L: Phalloidin, M: Glutamic acid, and N: Bovine albumin. +: positively charged cargos, +/−: zwitterionic cargos, ©: neutral cargo, and −: negatively charged cargos.

The present invention provides a use of a boron cluster as transmembrane carrier to transport a bioactive molecule across a membrane of a cell or vesicle, wherein the boron cluster comprises at least one hydrogen atom or alternatively at least one halogen atom, and the bioactive molecule is cationic, zwitterionic or not charged, so that the bioactive molecule is not negatively charged.

The essence of the present invention is therefore that different molecules can be transported into (and out of) vesicles or cells via boron clusters. It could be shown that boron clusters can function as a new class of membrane transporters. Boron clusters are therefore suitable for transporting other molecules through the membrane of cells or vesicles, without the requirement of a covalent attachment ("conjugation") between the transporter and the other molecule.

Advantages of boron clusters over the amphiphilic transporters used in the state of the art are good water solubility, broad applicability ("broadband"), and they do not precipitate the agents when added to the solution. They can be chemically modified and are accessible on a large scale.

Antibiotics, biocides or other drugs can thus be transported more readily into cells and their effect can thus be enhanced. In the same way, dyes can be transported into cells via boron clusters, which means that otherwise disadvantageous methods or reagents can be avoided. Boron clusters can be used to transport peptides, drugs such as antibiotics, dyes, proteins and other molecules, especially positively charged molecules, into the interior of vesicles (liposomes) or into cells. The vesicles may be used as membrane models. The transport of dyes and antibiotics is in particular possible; boron clusters can thereby be used to bypass antibiotic resistance. The use of the boron clusters of the present disclosure can thus be non-therapeutic or therapeutic.

The further advantages of the boron clusters include, most importantly, their potential to facilitate or bypass their endosomal escape and their broad cargo scope; the latter ranges from the protein protamine to arginine- and even lysine-containing charged peptides, to neutral cyclopeptides, to low-molecular weight analytes and drugs such as selected antibiotics.

In contrast to the conventional cationic, amphiphilic, and encapsulating carriers, boron clusters are highly water-soluble and do neither encapsulate nor tend to form nanoscale aggregates with their corresponding cargo. This leads commonly to complexation and precipitation with the compounds used in the state of the art.

Their effectiveness in inducing endosomal release, their biocompatibility, the transferability of their activity from vesicles to cells, and their broad cargo scope, which includes the delivery of impermeable small and neutral molecules, peptides, and proteins, differentiates them from known carriers and amphiphilic counterion activators. Boron clusters act as transmembrane carriers and, at the same time, counterion activators. The transferability of the carrier activity from vesicles to live cells, the high water solubility of the clusters (and their salts), insensitivity to membrane potential changes, the full retention of biological activity upon inversion of the sequence of cargo-carrier addition, are added assets that amphiphilic carriers have been lacking.

Membranes of living cells can also be penetrated and the compounds used are not cytotoxic and can therefore be used for living cells. The transport observed in the vesicles, which is induced by the boron clusters, is therefore also transferable to living cells respectively is also observed therein.

A "transmembrane carrier" is understood as molecule that allows another molecule to traverse a membrane which the molecule would not or not sufficiently fast be able to traverse without the transmembrane carrier or with the help of a membrane transport protein.

A “bioactive molecule” is understood as any molecule that has an effect when transported in a cell; this may include peptides, drugs such as antibiotics, dyes and proteins.

A “membrane” may be understood as a sphere-shaped lipid layer that segregates an interior aqueous medium from an exterior aqueous solvent.

A “vesicle” may be understood as a synthetic unilamellar or multilamellar lipid bilayer structure that encapsulates an aqueous phase and that can be used as a cellular lipid bilayer model.

A “boron cluster” is understood as a molecule that is composed out of at least eight boron atoms. Usually, the molecular size of such a boron cluster is below 10 nm in any dimension. Clusters (or “cluster compounds”) are furthermore delimited from nanoparticles, as clusters are always soluble (in suitable media) and do not show a Tyndall effect. Furthermore, “multinuclear boron clusters”, including “binuclear boron clusters”, are known. Binuclear boron clusters, for example, consist of two of the above described (mononuclear) boron clusters, which are connected by a metal atom, for example, cobalt, to form a such complex. A boron cluster may consist of a boron cluster core and optionally a pendant group.

The “boron cluster core” is a part of a molecule that includes boron atoms arranged in a polyhedral shape and any atoms required for saturation of the boron valences excluding pendant groups. In particular, boron, hydrogen, halogens (X), and methyl groups (—$CH_3$) may be part of a boron cluster core. In case of multinuclear boron clusters, also the connecting metal atom is seen as a part of the boron cluster core.

A “pendant group” is understood as any group and thus a part of a molecule which is linked to the boron cluster core, in particular covalently linked, and is not a hydrogen (H), a halogen (X), or a methyl group (—$CH_3$). Pendant groups do not include the bioactive molecule to be transported across a membrane.

Boron cluster chemistry is dominated by icosahedrally shaped cages (see Assaf et al. ChemPhysChem 2020, 21, 97-976), which can be exemplified by closo-$B_{12}H_{12}^{2-}$. Larger clusters (“fused clusters”) can be formally obtained by their mutual fusion. The closo,closo-$[B_{21}H_{18}]^-$ ion is an example of shared icosahedral moieties with three joint vertices. The COSAN ion (COBalt SANdwich, $Co(C_2B_9H_{11})^{2-}$) represents another way of fusion, i.e., via a single vertex and an inner cobalt atom.

The use of the boron cluster comprising at least one hydrogen atom and the use of a boron cluster comprising at least one halogen atom mentioned above are alternative solutions. The use of both boron clusters is based on the surprising finding that boron clusters are suitable for transporting other molecules through the membrane of cells or vesicles and can therefore function as a new class of membrane transporters.

In one embodiment, the boron cluster comprises a cluster structure of the formula $[B_aC_bR_dH_e]^{p-}$, wherein B represents boron, C represents carbon, R represents an organic group or a group comprising one or more heteroatoms, and H represents hydrogen, wherein a is 8 to 22, b is 0 to 4, d is 0 to 26 and e is 1 to 26, wherein d+e is 8 or greater but no greater than a+b and p is 1 to 4, wherein R may be the same or different groups, and R may be optionally linked to the remainder of the molecule by a linker.

In one alternative embodiment, the boron cluster comprises a cluster structure of the formula $[B_aC_bX_cR_d]^{p-}$, wherein B represents boron, C represents carbon, X represents a halogen, and R represents an organic group or a group comprising one or more heteroatoms, wherein a is 8 to 22, b is 0 to 4, c is 1 to 26, and d 0 to 26, wherein c+d is 8 or greater but no greater than a+b, and p is 1 to 4, wherein R may be the same or different groups, R may be optionally linked to the remainder of the molecule by a linker, and X may be the same or different halogens.

In a further embodiment, the boron cluster is comprised in an aqueous solution which additionally comprises the membrane and the bioactive molecule, wherein the membrane is part of a cell or a vesicle so that a transport of the bioactive molecule inside of the cell or the vesicle occurs.

The boron clusters of the present invention can be used to transport a bioactive molecule from the aqueous solvent through the membrane into the cell or vesicle. It is of course also possible to transport the bioactive molecule from the cell or vesicle into the aqueous solvent using the boron cluster. The aqueous solvent is part of the aqueous solution, whereby the solution contains at least the aqueous solvent, the bioactive molecule, the boron cluster and the cell or vesicle.

In yet another embodiment, the boron cluster comprises a cluster structure of the formula $[B_aC_bX_cR_dH_e]^{p-}$, wherein B represents boron, C represents carbon, X represents a halogen, R represents an organic group or a group comprising one or more heteroatoms, and H represents hydrogen, wherein a is 8 to 22, b is 0 to 4, c is 0 to 26, d is 0 to 26, and e is 0 to 26, wherein one of c and e is at least 1, c+d+e is 8 or greater but no greater than a+b, and p is 1 to 4, wherein R may be the same or different groups, R may be optionally linked to the remainder of the molecule by a linker, and X may be the same or different halogens.

According to another embodiment, a is 8 to 15, b is 0 to 2, c is 0 to 17, d is 0 to 17, and e is 0 to 17, wherein c+d+e is 8 or greater but no greater than a+b, and p is 1 to 4.

In one embodiment, the cluster structure comprised in the boron cluster is partially, mostly or completely saturated with halogen atoms (X). “Partially, mostly or completely saturated with halogen atoms” is understood as the cluster structure comprising at least 1, 5, 8, 10, 11 or 12 halogen atoms. Alternatively, it is understood as comprising a share of at least 8%, at least 70%, at least 80%, at least 90% or 100% of halogen atoms out of all atoms which are directly covalently linked to the carbon or boron atoms, which are part of the cluster structure and also comprised in the boron cluster core.

In an alternative embodiment, the cluster structure comprised in the boron cluster is partially, mostly or completely saturated with hydrogen atoms (H). “Partially, mostly or completely saturated with hydrogen atoms” is understood as the cluster structure comprising at least 1, 5, 8, 9, 10, 11 or 12 hydrogen atoms. Alternatively, it is understood as comprising a share of at least 8%, at least 70%, at least 81%, at least 90% or 100% of hydrogen atoms out of all atoms which are directly covalently linked to the carbon or boron atoms, which are part of the cluster structure and also comprised in the boron cluster core.

In a further embodiment, the cluster structure comprised in the boron cluster, which is also comprised in the boron cluster core, comprises asides methyl groups no carbon atoms. In another embodiment, the cluster structure comprised in the boron cluster comprises asides methyl groups a share between 15% and 20% of carbon atoms out of all carbon and boron atoms which are part of the cluster structure and which are also comprised in the boron cluster core.

In one embodiment, R is a C1 to C20 organic group with or without heteroatoms.

In another embodiment, R is a C1 to C20 organic group with heteroatoms.

In yet another embodiment, R is a C1 to C7 organic group with or without heteroatoms.

In one embodiment, R is a group with heteroatoms comprising 30 or less atoms overall.

A "group comprising heteroatoms" is understood as a group which comprises one or more heteroatoms and may or may not comprise carbon and/or hydrogen, wherein the heteroatom is or the heteroatoms can, for example, be selected from nitrogen, oxygen, sulfur, phosphorus, fluorine, bromine, chlorine and iodine. The group comprising heteroatoms may in particular be a nitrobenzoxadiazole (NBD) group, a nitro group (—$NO_2$), a sulfonic acid group (—$SO_3H$), a trimethylsilyl group [—$Si(CH_3)_3$] a trifluoromethyl group (—$CF_3$), an amine group (—$NH_2$, —NHR, —$NR_2$ or —$NR_3^+$), or a thiol group (—SH).

In another embodiment, the boron cluster comprises no pendant group or only one or more pendant groups with zero net charge, so that the entire net charge of the boron cluster is located in the boron cluster core. In a further embodiment, the net charge of the pendant group or the pendant groups is negative.

A "net charge" is understood to be the sum of all positive and negative formal charges of the atoms under consideration.

In a further embodiment, the pendant group is free of negatively charged or neutral polymerized groups. A "polymerized group" is understood to be a group with more than 10 repeating units. This includes in particular DNA, RNA, and polyalkylene glycols.

In one embodiment, the boron cluster is connected to the bioactive molecule to be transported across a membrane only via a weak, i.e., non-covalent, interaction. This allows a separation of the boron cluster and the bioactive molecule after the transport. A single boron cluster may thereby transport a large number of bioactive molecules.

In one embodiment, the boron cluster has more than one R group which can be the same or different.

The group R may optionally be connected with the boron atoms B or carbon atoms C of the boron cluster via a linker. In this case, the linker may, for example, be a thiomorpholine or an aminoalkyl group.

In one embodiment, R comprises a nitrobenzoxadiazole (NBD) group.

In yet another embodiment, p is 1 or 2 so that the boron cluster has a single or double negative charge.

In one embodiment, the cluster structure represents the entire boron cluster so that the cluster structure is not a part of a fused cluster.

In one embodiment, the boron cluster is not covalently linked to the bioactive molecule to be transported across the membrane so that only non-covalent interactions, namely the chaotropic effect as defined by Assaf and Nau in Angew. Chem. Int. Ed. 2018, 57, 13968-13981, are acting between the boron cluster and the bioactive molecule. Furthermore, the boron cluster and bioactive molecule can be stored separately, and a complex of boron cluster and bioactive molecule may be formed only in situ by weak interactions. The boron cluster can thus be used for various different bioactive molecules as required.

Avoiding conjugation between the molecule and the cluster eliminates the technical effort required to introduce covalent bonds, thus avoiding side reactions and the use of reactive chemicals.

In yet another embodiment, the boron cluster consists of a cluster core so that the boron cluster is free of a pendant group.

In one embodiment, the boron cluster is of globular or ellipsoidal shape.

Globular shape means in this context that the boron atoms are essentially arranged in a globular shape. Ellipsoidal shape means in this context that two globular boron cages are fused in a molecule to afford an ellipsoidally elongated structure. In particular, the term globular or ellipsoidal shape does not exclude pendant groups, such as an n-propoxy group as in the case of B2. B2 is thus also understood as a boron cluster of globular shape and CS3-CS6 are also understood as boron clusters of ellipsoidal shape.

In one embodiment, the boron cluster is a mononuclear boron cluster, a part of a multinuclear boron cluster, or a part of a fused boron cluster.

In an embodiment, the boron cluster can, for example, be $B_{12}Br_{12}^{2-}$, $B_{12}Br_{11}OC_3H_7^{2-}$, $B_{12}H_{11}NBD^-$, $B_{10}Br_{10}^{2-}$, (1,2-$C_2B_9HO_2$-3,3'-$Co^-$, (1,7-$C_2B_9H_{11})_2$-2,2'-$Co^-$, (1,2-$(CH_3)_2$-1,7-$C_2B_9H_9)_2$-3,3'-$Co^-$, (8-I-1,2-$C_2B_9H_{10}$)-(1'2'-$C_2B_9H_{11}$)-3,3'-$Co^-$, 8,8'-$Cl_2$-(1,2- $C_2B_9H_{10})_2$-3,3'-$Co^-$, or 8,8'-$I_2$-(1,2-$C_2B_9H_{10})_2$-3,3'-$Co^-$.

In one embodiment, the boron cluster is a fused boron cluster or a multinuclear boron cluster.

In a further embodiment, the boron cluster is negatively charged. In one embodiment, the membrane is part of a human cell, an animal cell, or a bacterial cell.

In yet another embodiment, the boron cluster is free of a guanidinium group.

In a further embodiment, the bioactive molecule is an antibiotic, so that the biological effect of the antibiotic is enhanced. The biological effect is understood as either killing or inhibiting the growth of bacteria and possibly an antiprotozoal effect.

In a further embodiment, the bioactive molecule is a proteolysis targeting chimera (PROTAC), so that the biological effect of the PROTAC is enhanced. The biological effect is understood as the enhanced uptake of the PROTAC which leads to the more efficient removal of specific (unwanted) proteins.

In a further embodiment, the bioactive molecule is an anticancer drug, so that the cell viability upon addition of the drug is decreased. The biological effect is understood as an enhanced permeation of the drug with the associated increased antineoplastic effect on cell growth.

In one embodiment, R comprises a nitrobenzoxadiazole (NBD) group.

In a further embodiment, p is 1 or 2 so that the boron cluster has a single or double negative charge.

Finally, the present invention is directed to a boron cluster as defined herein above for medical use, i.e., to enable transport of drugs, such as antibiotics, anticancer drugs and cytostatic drugs, across a membrane of a cell or vesicle. The present invention is thus in particular directed to a boron cluster as defined herein above for the treatment of a bacterial infection or cancer.

EXAMPLES

The synthesis of boron clusters and their chemistry is well developed due to their previous consideration for applications in boron neutron scattering therapy. Several boron clusters are commercially available. When boron clusters bear several or a single functional group, in particular OH, SH, or $NH_2$, they can be converted in many cases to derivatives, including organic derivates, by standard reaction procedures. Examples of such synthetic conversions of boron clusters under formation of organic derivatives are described in Assaf et al. Org. Lett. 2016, 18, 932-935, or El Anwar et al. Chem. Commun. 2019, 55, 13669.

A hydrophilic heptaarginine peptide (H-Trp-$Arg_7$-OH) which is unable to spontaneously translocate across neutral phosphocholine lipid vesicles in the absence of counterion activators was used as prototype for cationic cell-penetrating molecular scaffolds (peptides and polymers). The capability of boron clusters to activate the transport of the heptaarginine peptide (H-Trp-$Arg_7$-OH) was investigated first in large unilamellar vesicles (LUVs). The HPTS/DPX assay, that uses 8-hydroxypyrene-1,3,6-trisulfonate and p-xylene-bis-pyridinium, was implemented to monitor peptide-transport activation by the clusters. This assay not only reports on the potential of a synthetic carrier to transport the positively charged peptide into a vesicle, but also to shuttle the cationic quencher DPX to the outside.

Transport can accordingly be monitored, and the activator efficacy quantified, by a time-resolved fluorescence increase at different concentrations of the carrier.

HTPS emission was monitored during the sequential addition of the globular cluster carrier and peptide cargo; a strong detergent (Triton® X-100) was added at the end to affect vesicle lysis and complete dye release that allowed a normalization of the fluorescence intensity data. All chlorinated and brominated clusters were positive hits: They did not cause membrane disruption but instead acted as efficient transporters of heptaarginine across the lipid membrane of the vesicles.

For the highly active brominated cluster, a single short alkoxyl group ($B_{12}Br_{11}$O-propyl$^{2-}$) has little influence. On the other hand, when a 7-nitrobenzofurazan group is attached to the parent cluster ($B_{12}H_{11}$NBD-), efficient transport is observed.

In a further investigation it could be shown that boron clusters are suitable for the transport of neutral molecules, zwitterionic molecules and cationic molecules.

This was validated in vesicle transport experiments, which included targets which have not been previously accessible to other non-covalent synthetic carriers or counterion activators. The targets included singly charged, zwitterionic, and neutral biomolecules (such as acetylcholine and amino acids), vitamins, antibiotics, neuromuscular blocking agents and proteins. The cluster $B_{12}Br_{12}^{2-}$ (B1) transported all types of cargo (positive and neutral), with the exception of the negatively charged molecules (glutamate and albumin).

Most striking was the very fast transport kinetics, within seconds, for most cargo types, except for the neuromuscular blocking agents and phenylalanine.

The same trends were reproduced in transport efficiency with the smaller brominated cluster, B4 ($B_{10}Br_{10}^{2-}$) which proves that the cargo scope is transferable to different globular cluster carriers.

As a comparison, the same experiment was performed with an amphiphilic counterion activator from the state of the art, pyrene butyrate. None of the selected, zwitterionic or neutral, analytes (acetylcholine, tryptophan, ampicillin, vecuronium and phalloidin) showed any fluorescence response using the amphiphilic counterion activator of the state of the art. This demonstrates that the achieved transport phenomena and cargo scope are unique to borate clusters.

Such transport is also possible into the interior of living cells. For example, it was possible to transport the cell dye TRITC-phalloidin, which is known in cell biology as an excellent cell dye for the cytoskeleton, but which can only be transported into living cells with great effort. It could furthermore be shown that in one case an antibiotic could also be transported in bacteria (kanamycin), which increased its effectiveness.

Figure 4:
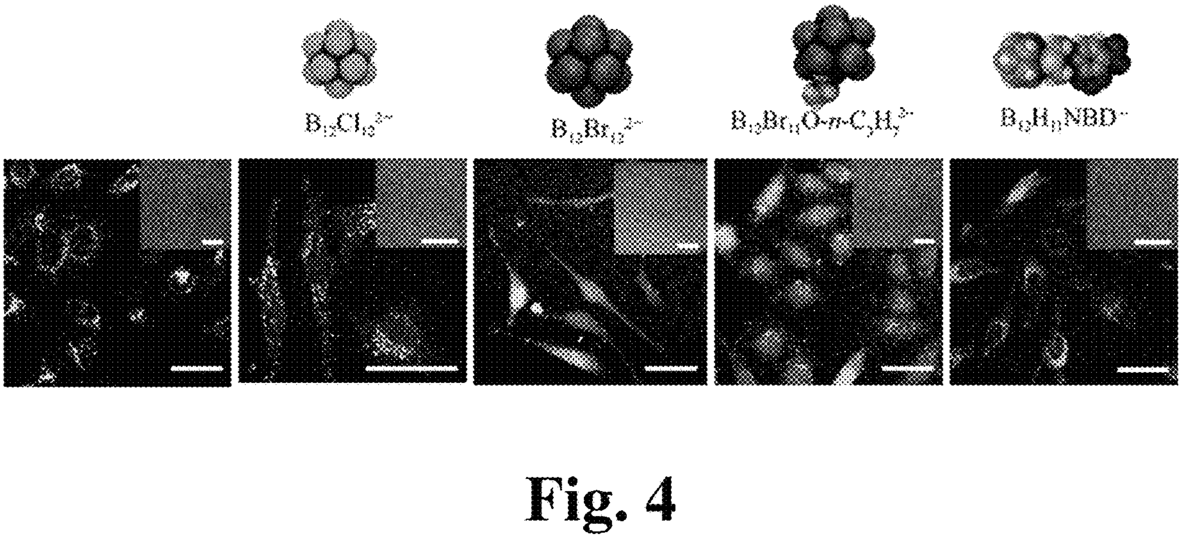
FIG. 4 shows TAMRA-octaarginine (Tm-$Arg_8$) endosomal escape promoted by different boron clusters (structures on top) in HeLa cells. Cells were incubated with 1 μM Tm-Arg8 and 0 (left picture) or 10 μM clusters diluted in HKR buffer for 1 hour, washed twice with HKR buffer, and imaged by confocal fluorescence microscopy; Images show TAMRA fluorescence (light gray) and the brightfield in the inset pictures; scale bars: 50 μm.

The potential of boron clusters to trigger the endosomal escape into live cells was first studied for oligocationic peptides as cargo. As a prototype, the octaarginine peptide labelled with carboxytetramethylrhodamine (Tm-$Arg_8$) was selected, which at low concentrations (i.e., 1 μM) enters cells by endocytosis and remains trapped in the intracellular compartments. The cytosolic delivery of Tm-$Arg_8$ was followed by confocal microscopy in the presence and absence of superchaotropic boron clusters (FIG. 4). In the absence of the clusters, cells incubated with Tm-$Arg_8$ showed punctate fluorescence of the penetrating peptide. In the presence of cluster B1-3, which had been identified as most active carriers in vesicles, enhanced peptide endosomal escape was observed as shown by the diffuse cytosolic fluorescence. Peptide delivery experiments with the fluorescent B3 cluster again showed significant peptide and cluster colocalization and heterogeneous intracellular distribution together with excellent peptide endosomal escape. The borate clusters furthermore showed very low cellular toxicity at different concentrations (as judged by MTT assay) also in the presence of 1 μM of the Tm-$Arg_8$ peptide.

Another area where carrier function is intensively being sought for is pharmaceutical drug delivery. As a proof-of-principle for pharmaceutical drug delivery, the potential of the prototype chaotropic boron cluster carrier, B1, was studied in reducing the minimum inhibitory concentration (MIC) of kanamycin A, a polycationic aminoglycoside antibiotic, in decreasing the IC50 value of dBET1, a proteolysis targeting chimera (PROTAC) proteins, and in decreasing the IC50 value of monomethyl auristatin F (MMAF), an antineoplastic drug.

Figure 5:
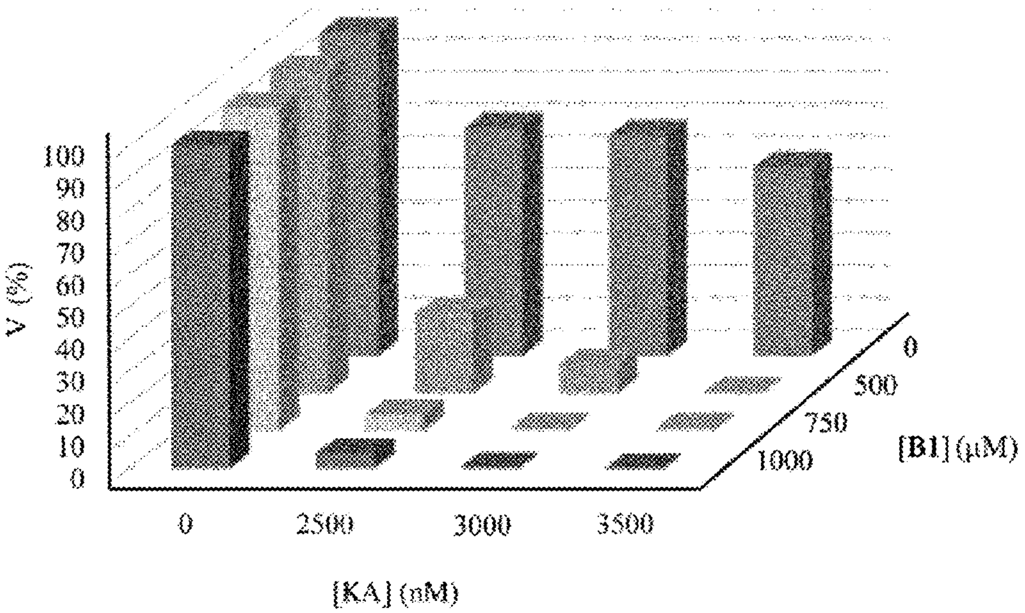
FIG. 5 shows B1-mediated kanamycin activity enhancement. Bar graphs (left) and time course (right) of *E. coli* Top10 viability in the presence of different concentrations of kanamycin monosulfate (0, 2500, 3000 or 3500 nM) and B1 (0, 500, 750 or 1000 μM) in LB broth at 37° C.; error bars (shown on the right) refer to the standard deviation (n=3; V (%): *E. coli* Top10 viability, [KA] (nM): Kanamycin A concentration in nanomolar.
Figure 5:
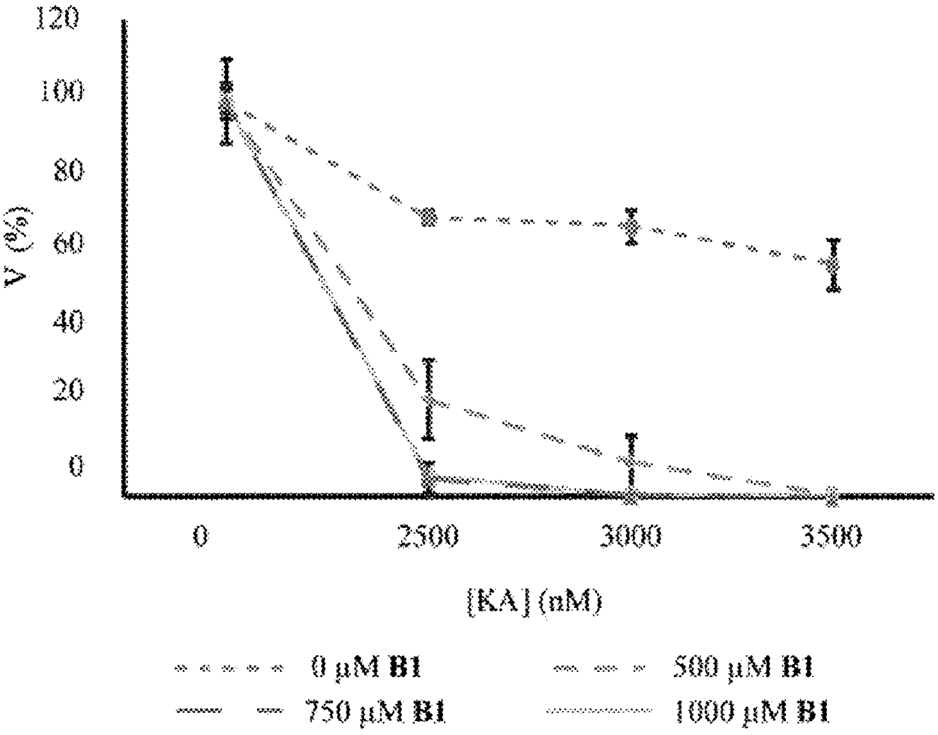
Figure 6:
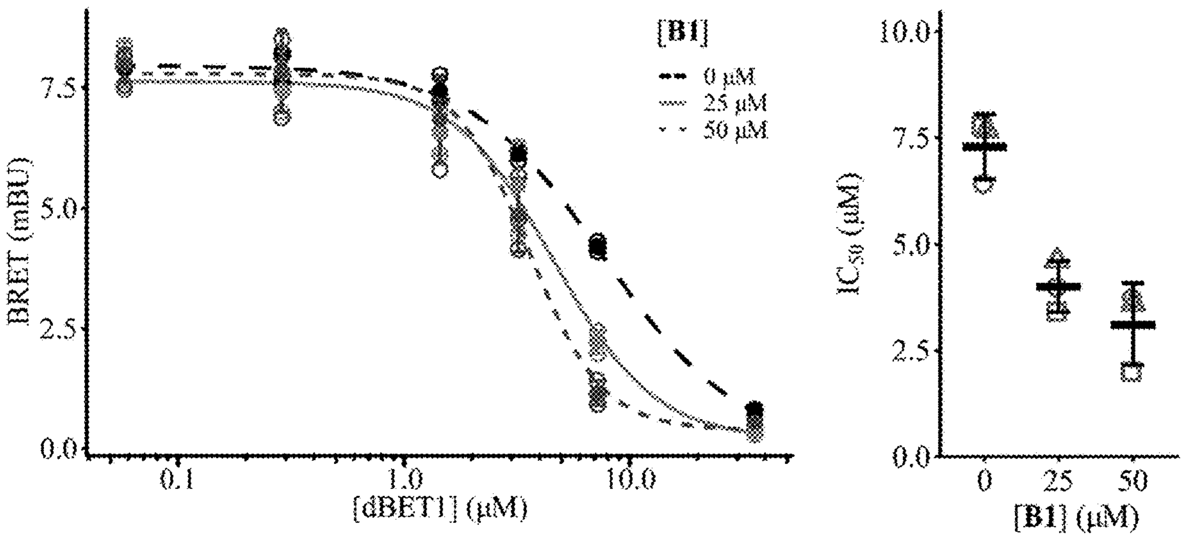
FIG. 6 shows: Left graph: Dose-response experiment for target engagement of a PROTAC (proteolysis targeting chimera, namely dBET1 [(6S)-4-(4-Chlorophenyl)-N-4-2-2-(2,6-dioxo-3-piperidinyl)-2,3-dihydro-1,3-dioxo-1H-isoindol-4-yloxyacetylaminobutyl-2,3,9-trimethyl-6H-thieno-3,2-f1,2,4-triazolo-4,3-a1,4-diazepine-6-acetamide], in the presence of 0, 25, and 50 μM B1. Solid points indicate means of three technical replicates; error bars indicate standard deviation; values were normalized to the controls without dBET1; BRET (in units of mBU) is the bioluminescence resonance energy transfer ratio. Right graph: Corresponding IC50 values (in micromolar) calculated with the CRBN Target Engagement assay. Crossbars and error bars indicate mean and standard deviation; values obtained in each experimental value are represented with a different shape.
Figure 7:
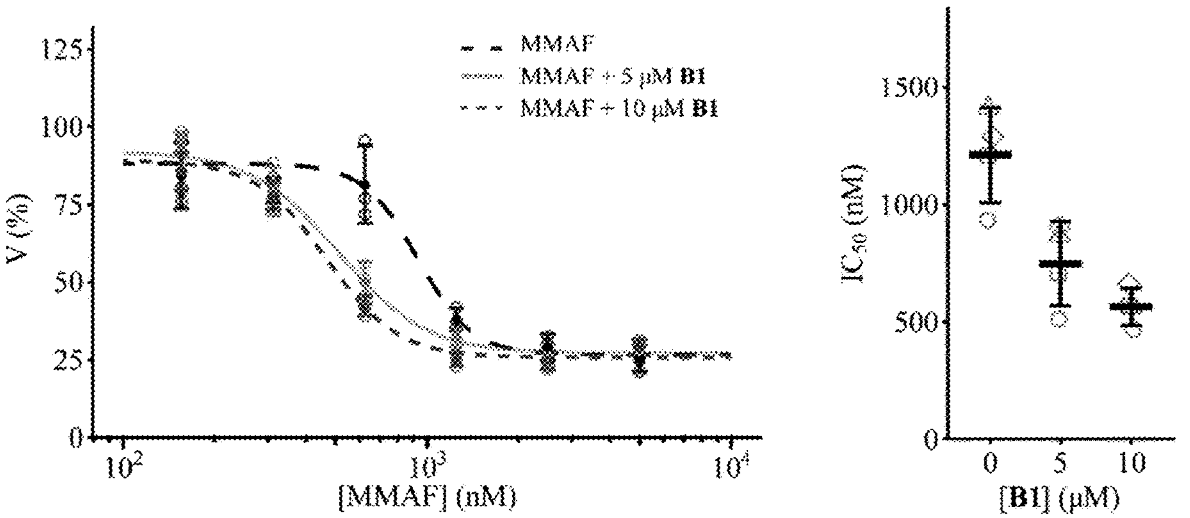
FIG. 7 shows: Left graph: Viability of HeLa cells (V percent): Viability of HeLa cells, after incubation with different doses of monomethyl auristatin F (MMAF) in the presence of 0, 5, and 10 μM B1. Solid points indicate the mean of three technical replicates; error bars indicate standard deviation. Right graph: Corresponding IC50 values (in nanomolar) of MMAF. Crossbar and error bars indicate mean and standard deviation, respectively, of four independent experiments (each one with technical triplicates); each experiment is represented with a different shape.
Figure 8:
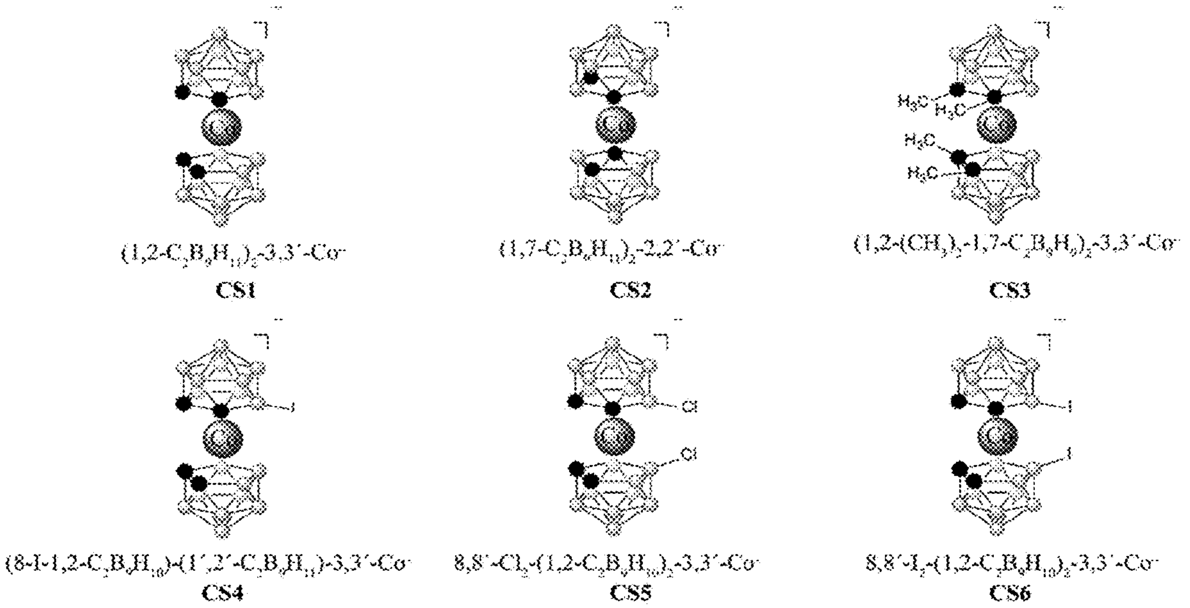
FIG. 8 shows chemical structures of COSAN cluster derivatives. (•=Boron, ◌ (grey)=Carbon).

For kanamycin A, effective passage through the cell membrane into the cytosol is essential to reach its intracellular targets. For example, the action of kanamycin A (3.5 μg/ml) on the Gram-negative *Escherichia coli* Top10 strain was investigated in the absence and presence of B1 (500 μM, compatible with mammalian cell survival). In the absence of the cluster, *E. coli* retained viability (60%), which disappeared almost completely (<5%) in the presence of the antibiotics carrier (FIG. 5). The enhanced antibiotic activity is attributed to the boron cluster's carrier potential as all other factors were left the same.

For dBET1, a PROTAC with known low permeability, it was shown that B1 enhances its activity. The internalization of this PROTAC in the absence and presence of the cluster was assessed by its ability to bind to the Cereblon E3 Ligase by using a NanoBRET™ TE Intracellular E3 Ligase Assay. Enhanced uptake of dBET1 was observed (factor 2-3 decrease in IC50 value).

For monomethyl auristatin F (MMAF, an antineoplastic drug with considerably lower permeability in comparison with other auristatins, B1 was found to effectively lower the IC50 value of MMAF (>factor of 2), as assessed through the viability of HeLa cells.

Also fused boron clusters and multinuclear boron clusters were successfully used as transporters for a bioactive molecule through a membrane.

Also iodinated boron clusters, in particular partially iodinated boron clusters, were successfully used as active clusters, and compounds CS4 or CS6 and the larger clusters such as CS1 or CS2 (COSAN clusters).

The present invention is not limited to embodiments described herein; reference should be had to the appended claims.

What is claimed is:

1. A method of treating cancer in a subject in need thereof, the method comprising:

providing an anticancer drug which is cationic, zwitterionic or not charged;

providing a halogenated boron cluster, wherein, the halogenated boron cluster has a globular shape or an ellipsoidal shape, the halogenated boron cluster is a mononuclear halogenated boron cluster, and the halogenated boron cluster is free of a pendant group, the pendant group being defined as any group which is linked to a core of the halogenated boron cluster except for hydrogen (H), a halogen (X), a methyl (—$CH_3$), and/or the anticancer drug;

mixing the halogenated boron cluster and the anticancer drug so that the halogenated boron cluster and the anticancer drug together form a non-covalent complex mixture; and administering the non-covalent complex mixture to the subject in need thereof so that the boron cluster acts as a transmembrane carrier to transport the anticancer drug across a membrane of a cell or a vesicle in the subject in need thereof.

2. The method as recited in claim 1, wherein the halogenated boron cluster has the formula $[B_aC_bX_cR_d]^{p-}$, wherein, B represents boron, C represents carbon, X represents a halogen, R represents an organic group or a group comprising one or more heteroatoms, a is 8 to 22, b is 0 to 4, c is 1 to 26, d is 0 to 26, c+d is 8 or greater but no greater than a+b, p is 1 to 4, and R is a same group or different groups.

3. The method as recited in claim 1, wherein the halogenated boron cluster is a cluster structure having the formula $[B_aC_bX_cR_dH_e]^{p-}$, wherein, B represents boron, C represents carbon, X represents a halogen, R represents an organic group or a group comprising one or more heteroatoms, H represents hydrogen, a is 8 to 22, b is 0 to 4, c is 0 to 26, d is 0 to 26, e is 0 to 26, one of c and e is at least 1, c+d+e is 8 or greater but no greater than a+b, p is 1 to 4, and R is a same group or different groups.

4. The method as recited in claim 1, wherein the halogenated boron cluster is $B_{12}Br_{12}^{2-}$, $B_{12}Br_{11}OC_3H_7^{2-}$, $B_{10}Br_{10}^{2-}$, (8-I-1,2-$C_2B_9H_{10}$)-(1'2'-$C_2B_9H_{11}$)-3,3'-$Co^-$, 8,8'-$Cl_2$-(1,2-$C_2B_9H_{10}$)$_2$-3,3'-$Co^-$, or 8,8'-$I_2$-(1,2-$C_2B_9H_{10}$)$_2$-3,3'-$Co^-$.

5. A method of treating cancer in a subject in need thereof, the method comprising:

providing an anticancer drug which is cationic, zwitterionic or not charged;

providing a halogenated boron cluster, wherein, the halogenated boron cluster has a globular shape or an ellipsoidal shape, the halogenated boron cluster is a mononuclear halogenated boron cluster, and the halogenated boron cluster is free of a pendant group, the pendant group being defined as any group which is linked to a core of the halogenated boron cluster except for hydrogen (H), a halogen (X), a methyl (—$CH_3$), and/or the anticancer drug; and administering each of the anticancer drug and halogenated boron cluster to the subject in need thereof, the halogenated boron cluster and the anticancer drug together forming a non-covalent mixture in situ so that the boron cluster acts as a transmembrane carrier to transport the anticancer drug across a membrane of a cell or a vesicle in the subject in need thereof.

* * * * *